United States Patent [19]

Bell

[11] Patent Number: 5,073,189

[45] Date of Patent: Dec. 17, 1991

[54] PESTICIDAL AQUEOUS FLOWABLE COMPOSITIONS

[75] Inventor: Mark Bell, Fareham, England

[73] Assignee: American Cyanamid Company, Stamford, Conn.

[21] Appl. No.: 467,819

[22] Filed: Jan. 19, 1990

Related U.S. Application Data

[63] Continuation of Ser. No. 153,530, Feb. 3, 1988, abandoned, which is a continuation of Ser. No. 780,525, Sep. 27, 1985, abandoned.

[51] Int. Cl.$^5$ .............................................. A01N 43/52
[52] U.S. Cl. .................................. 71/92; 71/DIG. 1; 71/120
[58] Field of Search ............................. 71/92, DIG. 1

[56] References Cited

U.S. PATENT DOCUMENTS

| | | | |
|---|---|---|---|
| 3,948,636 | 4/1976 | Marts | 71/112 |
| 4,188,487 | 2/1980 | Los | 71/92 |
| 4,227,912 | 10/1980 | O'Neal | 71/78 |
| 4,371,390 | 2/1983 | LeClair et al. | 71/93 |
| 4,461,641 | 7/1984 | Albildt et al. | 71/93 |

*Primary Examiner*—Glennon H. Hollrah
*Assistant Examiner*—B. Bembenick
*Attorney, Agent, or Firm*—John W. Hogan, Jr.

[57] ABSTRACT

The present invention provides chemically and physically stable pesticidal aqueous flowable compositions and a method for their preparation.

7 Claims, No Drawings

PESTICIDAL AQUEOUS FLOWABLE COMPOSITIONS

This is a continuation of application Ser. No. 153,530, filed Feb. 3, 1988, abandoned, which is a continuation of application Ser. No. 780,525, filed Sept. 27, 1985, abandoned.

BACKGROUND OF THE INVENTION

Flowable formulations of pesticides provide a method for applying water insoluble pesticides in an aqueous spray that avoids the handling of solid formulations such as wettable powders and granules. Aqueous based flowable compositions further avoid the use of organic solvent based flowables and emulsifiable concentrate compositions.

While aqueous flowable formulations of pesticides which are applied in aqueous sprays are highly desirable, gelling, caking and settling are major problems which are frequently encountered with this type of formulation.

These and other desirable features of flowable pesticide formulation and the difficulties encountered in preparing them are summarized in U.S. Pat. No. 4,348,385, which describe flowable pesticide formulations in selected solvents, which are miscible with water, and U.S. Pat. No. 4,071,617 describes aqueous based flowable pesticide formulations, which utilize vinyl alcohol/vinyl acetate polymers to obtain stability under mixing conditions.

It is an object of this invention to provide stable, aqueous flowable concentrate compositions of pesticides and a method for preparing said compositions.

SUMMARY OF THE INVENTION

The present invention is novel aqueous flowable compositions comprising 10% to 40% on a weight to volume basis of a finely ground particulate pesticide or mixture of pesticides suspended in an aqueous solution containing 5 to 40% by weight of a surfactant; 1.0% to 8.0% on a weight to volume basis of a wetting and/or dispersing agent and optionally containing 0.5% to 1.5% of an antifoam agent and 1% to 10% of an antifreezing agent.

Stable aqueous flowable concentrates of solid pesticides may be prepared without the use of additional thickening agents such as clays and soluble gums, which are normally used to prevent or slow settling, by utilizing aqueous solutions containing 5% to 40% by weight of surfactants which as 25% aqueous solutions have kinematic viscosities of about 5 to about 100 centistokes as the vehicle for the flowable composition. Surfactants giving kinematic viscosities in the above approximate range permit the use of sufficient quantities of said surfactants to obtain aqueous flowable concentrate compositions containing on a weight to volume basis 10% to 40% of solid finely ground pesticides, 1.0% to 8.0% of wetting dispersing agents and optionally 0.5% to 2.0% of antifoam agents, and 1% and 10% antifreezing agents such as glycols and alcohols, having viscosities of from 600 to 6,000 centipoises and preferably 1,000 to 3,500 entipoises as measured by a Brookfield viscometer, with a number 2 spindle at 6 rpm at 20° C., which resist settling of the solid components and do not gel. The kinmeatic viscosities of these surfactants measured as a 25% aqueous solution, allows the incorporation of high levels of surfactants in the final aqueous flowable pesticidal compositions, without causing them to become too viscous to process and use easily. The incorporation of high levels of surfactant provides the additional benefit that surfactants need not be incorporated during dilution of the flowable composition in a spray tank prior to application, making the compositions of this invention easier and safer to apply.

Surfactants suitable for use in compositions of the invention include polyoxyethylene alkyl phenols, polyoxyethylene styryl phenyl ether salts, polyoxyethylene fatty acids, polyoxyethylene alcohols and the like. Preferred surfactants for use in compositions of this invention are non-ionic, with the polyoxyethylene nonyl phenols containing 9 to 13 moles of ethoxylation and mixtures thereof being most preferred.

The pesticides that may be used in these stable concentrated flowables must be solids having essentially no significant water solubility (i.e., less than about 1.0 g/100 cc $H_2O$ at ambient temperature) and a particle size less than 200 $\mu$, usually in the range of 0.5 to 20 $\mu$. Preferably such particles will range in size from 0.5 $\mu$ to 5 $\mu$.

Pesticides, e.g., insecticides, fungicides, viricides, acaricides, herbicides, bactericides, and the like, having the above specifications may be used in the aqueous flowable concentrates of this invention. A representative example of a presently available pesticide which may be used in this invention is the recently introduced imidazolin-2-yl benzoate herbicide which is an isomeric mixture of methyl 6-(4-isopropyl-4-methyl-5-oxo-2-imidazolin-2-yl)-m-toluate and methyl 2-(4-isopropyl-4-methyl-5-oxo-2-imidazolin-2-yl-p-toluate. Stable aqueous flowable concentrates containing high concentrations i.e. 20% to 35% on a weight to volume basis of this herbicide may be readily prepared by milling an aqueous slurry containing 30% to 45% by weight of the herbicide, 2.0% to 4.0% by weight of a dispersing and/or wetting agent optionally containing 0.5 to 2.0% of an antifoam agent to the appropriate average particle size range of 0.5 to 20.0 microns and preferably less than 5 mirons. The aqueous flowable concentrate composition is then prepared by adding any additionally desired quantities of wetting and/or dispersing agents, and antifoam agents or antifreezing agents; and sufficient required water to total 100% of the final compsotiion, followed by the addition to the agitated aqueous slurry, of 5% to 35% of a surfactant which as a 25% aqueous solution has a kinematic viscosity of about 5 to about 100 centerstokes.

EXAMPLES 1-15

Preparation of stable aqueous flowable concentrate

A. Preparation of ground particulate aqueous slurry.

1. Calculate the quantities of each ingredient required and mix as follows: To a suitable vessel with fitted agitation, add all the water, then the antifoam agent if desired and then the wetting/dispersing agent, isomeric mixture of methyl 6-(4-isopropyl-4-methyl-5-oxo-2-imidazolin-2-yl)-m-toluate, and methyl 2-(4-isopropyl-4-methyl-5-oxo-2-imidazolin-2-yl-p-toluate. Gradually add the technical with vigorous high-shear agitation until a mobile slurry results. Continue high shear-mixign until the particle size is suitable for milling, avoiding air entrainment during mixing.

2. Pass the slurry through a wet-mill to give a suspension with particle size essentially 98% less than 5 microns.

3. Sample the milled slurry and analyse for active ingredient (% w/w).

B. Preparation of aqueous flowable concentrate.

1. Calculate the weight of milled slurry required for the final product and add it to a suitable vessel fitted with efficient agitation.

2. Calculate the extra quantities if any of wetting/dispersing agent, antifoam and antifreeze required in the final product and add them to the slurry and until the mixture is homogeneous.

3. Calculate the quantity of extra water required and add it to the vessel and mix until homogeneous.

4. Gradually add and dissolve the required amount of surfactant which as a 25% aqueous solution has a kinematic viscosity of 5 to 100 centerstokes and mix, with vigorous agitation, avoiding air entrainment.

5. Mix thoroughly until all the surfactant is dissolved and a smooth, uniform product is obtained.

Utilizing the above procedure yields the stable aqueous flowable compositions listed in Table I below.

TABLE I

| Aqueous flowable concentrate compositions | | | | | |
|---|---|---|---|---|---|
| Isomeric mixture of | Ex. 1 (g/l) | Ex. 2 (g/l) | Ex. 3 (g/l) | Ex. 4 (g/l) | Ex. 5 (g/l) |
| Methyl 6-(4-isopropyl-4-methyl-5-oxo-2-imidazolin-2-yl)-m-toluate and methyl 2-(4-isopropyl-4-methyl-5-oxo-2-imidazolin-2-yl-toluate | 340.0 | 283.3 | 340.0 | 283.3 | 226.7 |
| Polyethoxylated nonylphenol (11 molEO) viscosity 15 centerstokes as a 25% aqueous solution non-ionic surfactant | 120.0 | 160.0 | 150.0 | 200.0 | 200.0 |
| Wetting/dispersing agent (polyethoxylated polyarylphenol phosphate, neutralized with triethanolamine) | 40.0 | 40.0 | 40.0 | 40.0 | 40.0 |
| Silicone antifoam agent | 7.5 | 7.5 | 7.5 | 7.5 | 7.5 |
| Water (Balance) | 532.5 | 539.2 | 499.2 | 499.2 | 555.8 |
| Stability: | | | | | |

| Storage time | Example No. | Average percent recovery | | |
|---|---|---|---|---|
| | | 28° C. | 37° C. | 50° C. |
| One Month | 1-5 | 100.0 | 98.0 | 97.0 |
| Two Months | 3 & 5 | 99.0 | 98.0 | 98.0 |

TABLE II

| Polyoxyethylene nonylphenols suitable for use in compositions of the invention | |
|---|---|
| Average Ethoxylation (moles) | Kinematic viscosity (25% aqueous solution) centistokes |
| 9.5 | 102 |
| 9.5 | 87 |
| 10.0 | 53 |
| 10.0 | 43 |
| 10.0 | 22 |
| 10.5 | 18 |
| 11.0 | 30 |
| 12.0 | 13 |

EXAMPLE 6

Preparation of stable aqueous flowable concentrate compositions

Utilizing the procedure of examples and substituting the polyethoxylated nonylphenols having varying moles of ethoxylation and kinematic viscosities of 13 to 100 centistokes as a 25% aqueous solution listed in Table II below for the surfactant utilized in Example 1 yields stable aqueous flowable concentrate compositions of methl 6-(4-isopopryl-4-methyl-5-oxo-2-imidazolin-2-yl)-m-toluate and methyl 2-(4-isopropyl-4-methyl-5-oxo-2-imidazolin-2-yl-p-toluate.

EXAMPLE 7-8

Utilizing the procedures of examples 1-5 and substituting the mixed polyoxyethylene nonylphenol with 10 to 12 moles of ethoxylation and a polyoxyethylene styrylphenyl ether sulphate which as a 25% aqueous solution has a kinematic viscosity of about 8 centistokes, for the polyoxyethylene nonylphenols employes in those examples yields the stable aqueous flowable compositions listed in Table III below.

EXAMPLE 9-10

Utilizing the procedure of Examples 1-5, utilizing mixtures of herbicides yields the stable aqueous flowable compositions listed in Tablve IV below.

TABLE III

| Aqueous flowable concentrate compositions | | |
|---|---|---|
| Composition | Example 7 % w/v | Example 8 % w/v |
| Methyl 6-(4-isopropyl-4-methyl-5-oxo-2-imidazolin-2-yl)-m-toluate methyl 2-(4-isopropyl-4-methyl-5-oxo-2-imidazolin-2-yl-p-toluate | 33.1 | 33.1 |
| Wetting/dispersing agent polyoxyethylene glycol sulfate | 4.0 | 4.0 |
| Polyoxyethylene styrylphenylether sulfate | 11.25 | 3.0 |
| Polyoxyethylene nonylphenol 10-12 moles of ethoxylation | 0.0 | 11.5 |
| Ethylene glycol | 5.0 | 5.0 |
| Water | To 100% | To 100% |

TABLE IV

| Note: The following mixtures can also be prepared | | | |
|---|---|---|---|
| Composition | Example 8 % w/v | Example 9 % w/v | Example 10 % w/v |
| Methyl 6-(4-isopropyl-4-methyl-5-oxo-2-imidazolin-2-yl)-m-toluate methyl 2-(4-isopropyl-4-methyl-5-oxo-2-imidazolin-2-yl-p-toluate | 10.0 | 10.0 | 5.3 |
| N,N-dimethyl-N'-[4-(1-methylethyl)phenyl]urea | 25.0 | — | — |
| N'-(3-chloro-4-methylphenyl)-N,N-dimethylurea | — | 25.0 | — |

TABLE IV-continued

Note: The following mixtures can also be prepared

| Composition | Example 8 % w/v | Example 9 % w/v | Example 10 % w/v |
|---|---|---|---|
| N'-(3-chloro-4-methoxyphenyl)-N,N-dimethylurea | — | — | 32.0 |
| Polyoxyethylene styrylphenylether sulfate | 4.0 | 4.0 | 4.0 |
| Polyoxyethylene nonylphenol 11 moles of ethoxylation | 10.0 | 10.0 | 10.0 |
| Ethylene glycol | 8.0 | 8.0 | 8.0 |
| Silicone antifoam agent | 0.75 | 0.75 | 0.75 |
| Water | To 100% | To 100% | To 100% |

What is claimed is:

1. A pesticidal aqueous flowable concentrate composition comprising on a weight to volume basis 10% to 40% of a finely ground particulate mixture of pesticides wherien said mixture comprises methyl (6-(4-isopropyl-4-methyl-5-oxo-2-imidazolin-2-yl)-m-toluate and methyl 2-(4-isopropyl-4-methyl-5-oxo-2-imidazolin-2-yl)-p-toluate suspended in an aqueous solution, containing 5% to 40% by weight of a nonionic polyoxyethylene surfactant with about 9 to 13 moles of ethoxylation which as a 25% aqueous solution has a kinematic viscosity of about 5 to about 100 centistokes as the vehicle for the flowable composition wherein said composition is stable without thickening agents, clays, or soluble gums.

2. The pesticidal aqueous flowable concentrate composition according to claim 1, having a viscosity of 600 to 6,000 centipoises as measured by a Brookfield viscometer with a number 2 spindle, at 6 rpm, at 20° C., wherein the particle size of the pesticide is in the range of 0.5 to 20 microns.

3. The composition according to claim 2, wherein the particle size of greater than 95% of the pesticide is 5 microns or less; additionally containing on a weight to volume basis based on the total composition, 1% to 8.0% of a wetting/dispersing agent; 0.5 to 2.0% of an antifoam agent and 0.0 to 10% of an antifreezing agent.

4. The composition according to claim 3, wherein the surfactant is a polyoxyethylene nonylphenol.

5. The composition according to claim 4, having a viscosity of 1,000 to 3,500 centipoises as measured with a Brookfield viscometer with a number 2 spindle, at 6 rpm, at 20° C.

6. The composition according to claim 1 consisting essentially of 33.1% of an isomeric mixture of methyl 6(4-isopropyl-4-methyl-5-oxo-2-imidazolin-2-yl)-m-toluate and methyl 2(4-isopropyl-4-methyl-5-oxo-2-imidazolin-2-yl)-p-toluate, 4.0% of polyoxyethylene glycol sulfate, 11.25% of polyoxyethylene styrylphenylether sulfate 5.0% of ethylene glycol and the remainder water.

7. The composition according to claim 1 consisting essentially of 33.1% of an isomeric mixture of methyl 6(4-isopropyl-4-methyl-5-oxo-2-imidazolin-2-yl)-m-toluate and methyl 2(4-isopropyl-4-methyl-5-oxo-2-imidazolin-2-yl)-p-toluate, 4.0% of polyoxyethylene glycol sulfate, 11.25% of polyoxyethylene styrylphenylether sulfate, 11.5% of polyoxyethylene nonylphenol with 10-12 moles of ethoxylation, 5.0% of ethylene glycol and the remainder of.

* * * * *

UNITED STATES PATENT AND TRADEMARK OFFICE
CERTIFICATE OF CORRECTION

PATENT NO. : 5,073,189

DATED : December 17, 1991

INVENTOR(S) : Mark Bell

It is certified that error appears in the above-indentified patent and that said Letters Patent is hereby corrected as shown below:

In the claims, column 5, claim 1, line 20 should read:
"....methyl 6-(4-isopropyl-...."

Claim 1, column 5, line 21 should read:
"....4-methyl-5-oxo-2-imidazolin-2-yl)-m-toluate"

Claim 6, column 6, line 17 should read:
"6-(4-isopropyl...."

Claim 6, column 6, line 18 should read:
"....methyl 2-(4-isopropyl...."

Claim 6, column 6, line 19 should read:
"imidazolin-2-yl)-p-toluate,...."

Claim 7, column 6, line 26 should read:
"6-(4-isopropyl-4-methyl-5-oxo-2-imidazolin-2-yl)-m-"

Claim 7, column 6, line 27 should read:
"....methyl 2-(4-isopropyl...."

UNITED STATES PATENT AND TRADEMARK OFFICE
CERTIFICATE OF CORRECTION

PATENT NO. : 5,073,189
DATED : December 17, 1991
INVENTOR(S) : Mark Bell

It is certified that error appears in the above-indentified patent and that said Letters Patent is hereby corrected as shown below:

Claim 7, column 6, line 28 should read:
"imidazolin-2-yl-p-toluate,...."

Claim 7, column 6, line 29 should read:
"glycol sulfate, 3% of...."

Claim 7, column 6, line 32 should read:
"glycol and the remainder water."

Signed and Sealed this

Twenty-sixth Day of October, 1993

Attest:

BRUCE LEHMAN

Attesting Officer

Commissioner of Patents and Trademarks